United States Patent [19]

Nazre et al.

[11] Patent Number: 5,591,164
[45] Date of Patent: Jan. 7, 1997

[54] EXTERNAL FIXATION APPARATUS AND SYSTEM

[75] Inventors: Aniruddha A. Nazre, Warsaw; Elson B. Fish, Lakeville, both of Ind.

[73] Assignee: Zimmer, Inc., Warsaw, Ind.

[21] Appl. No.: 361,779

[22] Filed: Dec. 22, 1994

[51] Int. Cl.$^6$ .................................................. A61B 17/64
[52] U.S. Cl. .................................... 606/59; 606/54; 606/76
[58] Field of Search ..................................... 606/53, 54, 55, 606/56, 57, 58, 59, 60, 72, 73, 76

[56] References Cited

U.S. PATENT DOCUMENTS

| | | |
|---|---|---|
| 4,308,863 | 1/1982 | Fischer . |
| 4,365,624 | 12/1982 | Jaquet . |
| 4,535,763 | 8/1985 | Jaquet . |
| 4,584,995 | 4/1986 | Koeneman . |
| 4,620,533 | 11/1986 | Mears . |
| 4,624,249 | 11/1986 | Alvarex Cambras . |
| 4,747,400 | 5/1988 | Koeneman et al. . |
| 4,768,524 | 9/1988 | Hardy . |
| 4,784,125 | 11/1988 | Monticelli . |
| 4,889,111 | 12/1989 | Ben-Dov . |
| 4,893,618 | 1/1990 | Herzberg ................................. 606/54 |
| 4,895,141 | 1/1990 | Koeneman et al. ....................... 606/54 |
| 4,902,297 | 2/1990 | Devanathan ............................... 623/16 |
| 4,923,458 | 5/1991 | Fischer ....................................... 606/59 |
| 4,936,843 | 6/1990 | Sohngen .................................... 606/54 |
| 4,941,481 | 7/1990 | Wagenknecht ............................ 606/59 |
| 4,978,358 | 12/1990 | Bobyn ....................................... 623/16 |
| 4,978,360 | 12/1990 | Devanathan ............................... 623/66 |
| 5,021,054 | 6/1991 | Monfardini ............................... 606/54 |
| 5,067,954 | 11/1991 | Ilizavor ..................................... 606/58 |
| 5,087,258 | 2/1992 | Schewior .................................. 606/56 |
| 5,095,919 | 3/1992 | Monticelli ................................. 606/56 |
| 5,098,432 | 3/1992 | Wagenknecht ............................ 606/54 |
| 5,112,331 | 5/1992 | Miletich ..................................... 606/53 |
| 5,163,962 | 11/1992 | Salzstein .................................... 623/23 |
| 5,167,661 | 12/1992 | Wagenknecht ............................ 606/54 |
| 5,181,930 | 1/1993 | Dumbleton ............................... 623/23 |
| 5,192,330 | 3/1993 | Chang ....................................... 623/22 |
| 5,209,750 | 5/1993 | Stef ........................................... 606/54 |
| 5,219,363 | 6/1993 | Crowninshield ......................... 623/23 |
| 5,275,598 | 1/1994 | Cook ......................................... 606/54 |
| 5,350,378 | 9/1994 | Cole et al. ................................. 606/57 |

OTHER PUBLICATIONS

Zimmer Brochure, Fracture Management, Torus External Fixation System.

*Primary Examiner*—Guy V. Tucker
*Attorney, Agent, or Firm*—Todd A. Dawson

[57] ABSTRACT

The invention is directed to an apparatus for external fixation and stabilization of a fracture in a bone including a one-piece fixation rod, at least two fixation pins attachable to the bone, and at least two clamp assemblies. Each clamp assembly interconnects at least one fixation pin and the fixation rod, The fixation rod is compressible in an axial direction upon occurrence of axial loads typical to those experienced at the fracture, thereby allowing an axial compression loading to be placed on the bone at the fracture when the apparatus is in use. The fixation rod consists essentially of a non-homogeneous, i.e., composite, material.

9 Claims, 3 Drawing Sheets

EXTERNAL FIXATION APPARATUS AND SYSTEM

BACKGROUND OF THE INVENTION

1. Field of the invention

The present invention relates to an apparatus for external fixation and stabilization of a fractured bone, and, more particularly, to such an apparatus having a fixation rod interconnected to the fractured bone at a plurality of locations via a plurality of respective fixation pins.

2. Description of the related art

External fixation apparatus of known design are utilized for fixating and stabilizing fractured bones. While fixation apparatus and systems have undergone considerable evolutionary changes over the years, they all rigidly hold the sections of a broken bone in alignment throughout the healing process. Fixation devices may be in the form of a relatively crude splint or cast, or a more modern and sophisticated system involving surgical fixation pins secured to an external fixation rod, or the Ilizarov system well known to those skilled in the art.

Conventional fixation systems currently on the market may include a hexagonal fixation bar used to interconnect and rigidly secure a plurality of fixation pins inserted into the fractured bone at various points, with each fixation pin being retained within a clamp secured to the fixation rod. Each clamp is installed onto the fixation rod by sliding the clamp over one end or the other and tightening one or more nuts when the clamp is in its desired longitudinal position on the rod. An example of such a system is disclosed in U.S. patent application Ser. No. 08/017,933, entitled "EXTERNAL FIXATION APPARATUS" filed Feb. 16, 1993, the disclosure of which is expressly incorporated herein by reference.

A problem with conventional designs is that they are constructed of a metal having a known modulus of elasticity. The modulus of elasticity does not change for a particular metal, regardless of whether the selected metal is a commercially pure or alloy material. For example, stainless steel has a modulus of elasticity of about $30 \times 10^6$ PSI; commercially pure titanium and titanium alloy have a modulus of elasticity of about $16 \times 10^6$ PSI; aluminum has a modulus of elasticity of about $10 \times 10^6$ PSI; and magnesium has a modulus of elasticity of about $8-9 \times 10^6$ PSI. The modulus of elasticity in the axial direction of the fixation rod relates to the amount of elastic movement possible within the fixation rod in an axial direction for a given axial load. Movement of the fixation rod in the axial direction, in turn, relates to the amount of axial movement at the fracture site of the bone. It is generally accepted in the art that an increased axial movement at the fracture site theoretically improves the fracture healing process. However, for a material such as stainless steel having a high modulus of elasticity, the loads experienced at the fracture site are not sufficient to elastically deform the fixation bar. Accordingly, no movement of the bone in an axial direction at the fracture site occurs, with resultant detrimental effects on the healing process.

One known method of increasing the load on the bone at the fracture site is to loosen the clamp assemblies attached to the fixation rod and slide the clamp assemblies in an axial direction along the fixation rod in a direction toward the fracture site. However, this results in a constant load being placed on the bone at the fracture site rather than inducing axial movement of the bone sections on each side of the fracture site, since the fixation rod does not elastically move under such typical loads.

Another problem is that the step between each respective modulus of elasticity for conventional fixation bars constructed of different metals is quite large. For example, the step between the modulus of elasticity for stainless steel and titanium is about $14 \times 10^6$ PSI (30-16). Since stainless steel and titanium are the two most commonly used materials for conventional fixation rods, the modulus of elasticity is either $30 \times 10^6$ PSI or $16 \times 10^6$ PSI, without the ability to select a material having a modulus of elasticity disposed therebetween.

A still further problem is that clamp assemblies of conventional design are made to accept a fixation rod of a particular exterior geometric configuration. When a fixation rod constructed of one metal is substituted for a fixation rod constructed of another metal, the exterior geometry must remain the same in order to attach to the clamp assemblies. However, as the axial compression stiffness of the fixation rod changes as a result of the change in the modulus of elasticity, the bending stiffness and torsional stiffness also change as a result of using a different material. Therefore, using a metal which has a lower modulus of elasticity to improve the axial loading on the bone may result in other detrimental affects such as twisting or bending of the fixation rod, thereby allowing movement of the bone sections in a radial direction at the fracture site.

What is needed in the art is an external fixation apparatus which includes a plurality of fixation rods having an axial compression stiffness which may be varied, while maintaining a relatively constant torsional and bending stiffness.

SUMMARY OF THE INVENTION

The present invention provides a plurality of fixation rods for an external fixator which have a varying axial compression stiffness from one rod to another, and a relatively constant torsional and bending stiffness from one rod to another.

The invention comprises, in one form thereof, an apparatus for external fixation and stabilization of a fracture in a bone, including a one-piece fixation rod, at least two fixation pins attachable to the bone, and at least two clamp assemblies. Each clamp assembly interconnects at least one fixation pin and the fixation rod. The fixation rod is compressible in an axial direction upon occurrence of axial loads typical to those experienced at the fracture, thereby allowing an axial compression loading to be placed on the bone at the fracture when the apparatus is in use.

The invention comprises, in another form thereof, an external fixator assembly which is used to fixate and stabilize a fracture in a bone, and which includes a fixation rod comprising an elongated rod having a substantially constant cross-section and consisting essentially of a non-homogeneous material.

An advantage of the present invention is that a plurality of rods are provided which have respective axial compression stiffnesses.

Another advantage is that the axial compression stiffness varies from rod to rod while the torsional and bending stiffnesses remain relatively the same from rod to rod.

Yet another advantage is that the fixation rod of the present invention is lightweight in comparison with conventional designs.

A further advantage is that a plurality of fixation rods having respective predetermined axial compression stiffnesses are utilized, thereby allowing selective axial loads to be placed on the bone at the fracture site, dependent on the particular fixation rod utilized.

A still further advantage is that the axial compression stiffness of a particular fixation rod may be modified by changing the internal, non-homogeneous construction thereof.

An additional advantage is that the fixation rods of the present invention are X-ray and MRI radiolucent.

Another advantage is that the exterior geometry of the fixation rods is the same as a conventional design, thereby allowing use with conventional clamp assemblies.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 1:
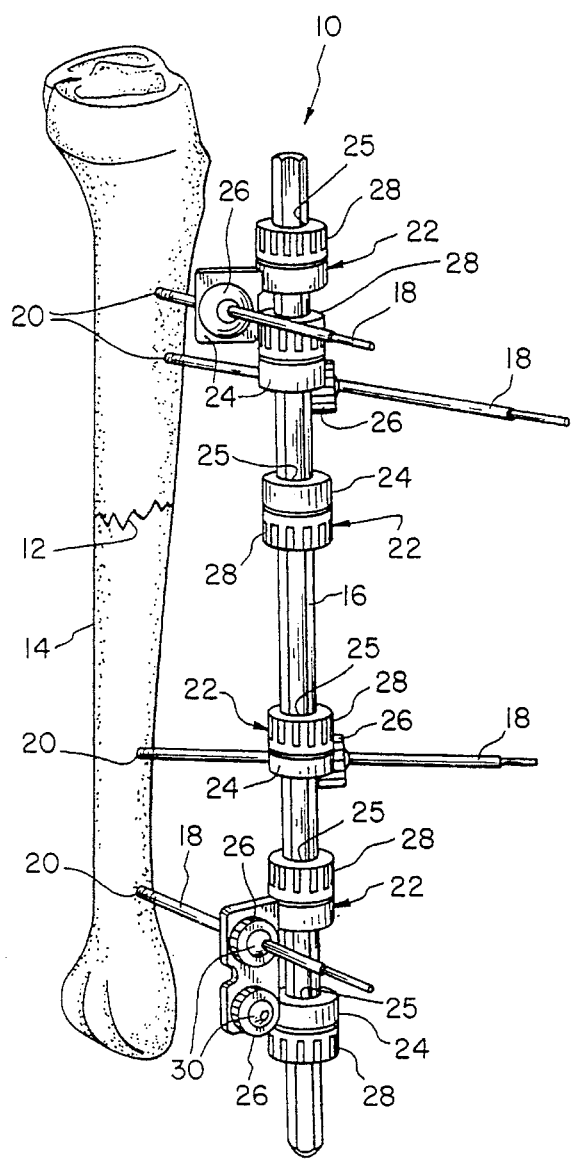
FIG. 1 is a perspective view of one embodiment of the external fixator assembly of the present invention, when fastened to a fractured bone.

Referring now to the drawings and more particularly to FIG. 1, there is shown an external fixator assembly 10 which is used to fixate and stabilize fracture 12 of bone 14. External fixator assembly 10 includes a hexagonal fixation rod 16, to be described in more detail hereinafter, which is disposed generally parallel with bone 14. Fixation pins 18 include respective threaded ends 20 which are screwed into bone 14 at desired locations. A plurality of clamp assemblies 22 respectively interconnect at least one fixation pin 18 with fixation rod 16. Each clamp assembly 22 includes a body 24 with at least one first opening 25 for receiving fixation rod 16, and at least one second opening for receiving fixation pin 18. Body 24 is adapted to threadingly receive a retaining nut 26 associated with a fixation pin 18, and a retaining nut 28 associated with fixation rod 16. Each of retaining nuts 26 and 28, in known fashion, engage collets 30 which lock clamp assembly 22 to fixation pins 18 and fixation rods 16, respectively.

In the embodiment shown, the lowermost clamp assembly 22 has two retaining nuts 26, but only engages one fixation pin 18. It is to be understood, however, that a clamp assembly 22 having two retaining nuts 26 can engage more than one fixation pin 18 if desirable for a particular application.

Figure 2:
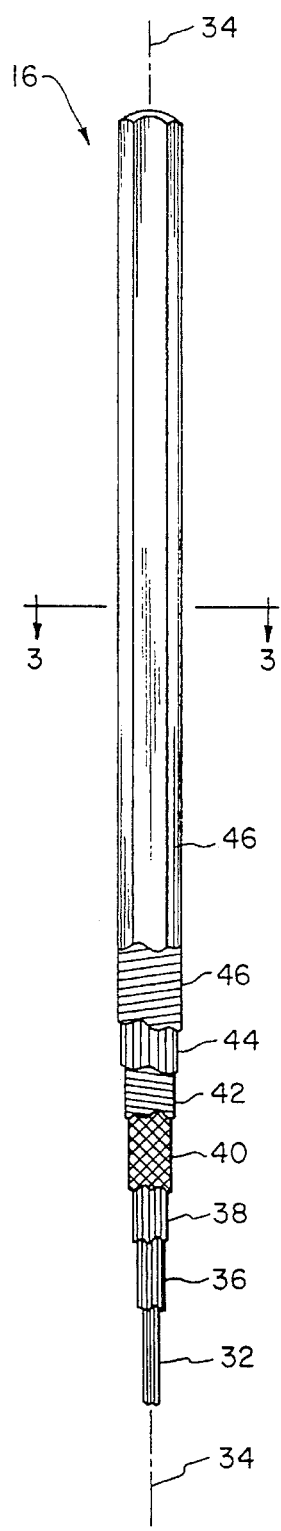
FIG. 2 is a layered side view of the fixation rod shown in FIG. 1.
Figure 3:
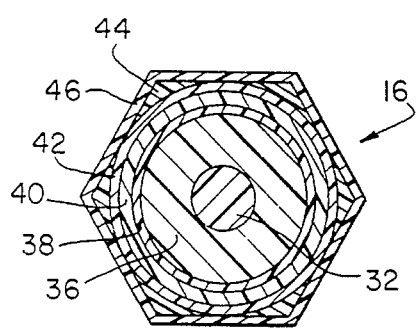
FIG. 3 is a sectional view taken along line 3—3 of FIG. 2.

Referring now to FIGS. 2 and 3, fixation rod 16 of the present invention is shown in greater detail. Fixation rod 16 shown in FIGS. 1–3 includes seven separate laminae bound together by a resin, which together form a solid fixation rod. The first lamina 32 includes polyester fibers which are oriented at a zero degree angle relative to a longitudinal axis 34 of fixation rod 16. That is, polyester fibers 32 are oriented generally parallel to longitudinal axis 34. Second lamina 36 includes glass fibers which are oriented at a zero degree angle relative to longitudinal axis 34. Third lamina 38 includes polyester fibers oriented at a zero degree angle relative to longitudinal axis 34. Fourth lamina 40 includes carbon fibers which are woven together and oriented at respective 45° angles relative to longitudinal axis 34. Fifth lamina 42 includes glass fibers oriented at an 82° angle relative to longitudinal axis 34. Sixth lamina 44 includes glass fibers oriented at a zero degree angle relative to longitudinal axis 34. Seventh lamina 46 includes polyester fibers oriented at an 82° angle relative to longitudinal axis 34. Seventh lamina 46 and fifth lamina 42 are disposed at opposite angles relative to longitudinal axis 34. Laminae 32, 36, 38, 40, 42, 44 and 46 are positioned concentrically about longitudinal axis 34, as shown in FIG. 3.

The fixation rod described above with reference to FIGS. 2 and 3 includes seven laminae with the respective fiber orientations as indicated. The orientation of the fibers within each lamina making up the composite fixation rod determine the torsional, bending, and axial compression stiffness of the rod. By varying the angles of the fibers in one or more layers with respect to the longitudinal axis of the rod, it is possible to modify the stiffness of the rod in a particular desired direction. For example, in the embodiment shown, fourth lamina 40 including woven carbon layers disposed at a 45° angle relative to longitudinal axis 34 primarily control the torsional stiffness of fixation rod 16. By varying the angle of the carbon fibers in fourth lamina 40, or the angle of the fibers in other laminae, it is possible to affect the torsional, bending and axial compression stiffnesses of fixation rod 16.

FIGS. 4–7 illustrate stiffnesses of five different composite fixation rods in the torsional, medial/lateral bending, anterior/posterior bending and axial compression directions. Each of the fixation rods is a hexagonal rod having dimensions of 0.495±0.005 inch across the flats and 0.577 from corner to corner. The following tables set forth the number of laminae making up each rod illustrated in FIGS. 4–7, the type of material for each lamina, the moment of inertia (I) for each lamina and the orientation of the fibers within each lamina relative to the longitudinal axis of the rod:

| Lamina No. | Material | I | Orientation |
|---|---|---|---|
| | Rod A: | | |
| 1 | Polyester | 2.94E-5 | 0° |
| 2 | Fiberglass | 4.39E-4 | 0° |
| 3 | Polyester | 8.68E-4 | 0° |
| 4 | Carbon | 8.19E-4 | ±45° |
| 5 | Fiberglass | 2.01E-4 | +82° |

-continued

| Lamina No. | Material | I | Orientation |
| --- | --- | --- | --- |
| 6 | Fiberglass | 1.19E-3 | 0° |
| 7 | Polyester | 2.05E-4 | -82° |
| Rod B: | | | |
| 1 | Polyester | 5.49E-4 | 0° |
| 2 | Fiberglass | 4.27E-4 | 0° |
| 3 | Polyester | 3.58E-4 | 0° |
| 4 | Carbon | 8.21E-4 | ±45° |
| 5 | Fiberglass | 2.01E-4 | +82° |
| 6 | Fiberglass | 1.19E-3 | 0° |
| 7 | Polyester | 2.06E-4 | -82° |
| Rod C (Hollow with plugged ends; I.D. = 0.324): | | | |
| 1 | Fiberglass | 4.38E-4 | ±45° |
| 2 | Carbon | 7.15E-4 | ±45° |
| 3 | Fiberglass | 1.58E-4 | +82° |
| 4 | Fiberglass | 1.69E-3 | 0° |
| 5 | Polyester | 2.05E-4 | -82° |
| Rod D (Hollow with plugged ends): | | | |
| 1 | Fiberglass | 3.68E-4 | ±70° |
| 2 | Carbon | 8.09E-4 | ±45° |
| 3 | Fiberglass | 1.98E-4 | +82° |
| 4 | Fiberglass | 1.25E-3 | 0° |
| 5 | Polyester | 2.05E-4 | -82° |
| Rod E (Hollow with plugged ends): | | | |
| 1 | Fiberglass | 3.76E-4 | ±70° |
| 2 | Carbon | 8.21E-4 | ±45° |
| 3 | Fiberglass | 2.01E-4 | +82° |
| 4 | Fiberglass | 1.19E-3 | 0° |
| 5 | Fiberglass | 2.06E-4 | -82° |

The fiberglass listed in the above tables for fixation rods A–E is an E fiberglass; the carbon has a tensile modulus of about $32 \times 10^6$ PSI; and the polyester has a tensile strength of about $1.4 \times 10^6$ PSI.

Figure 4:
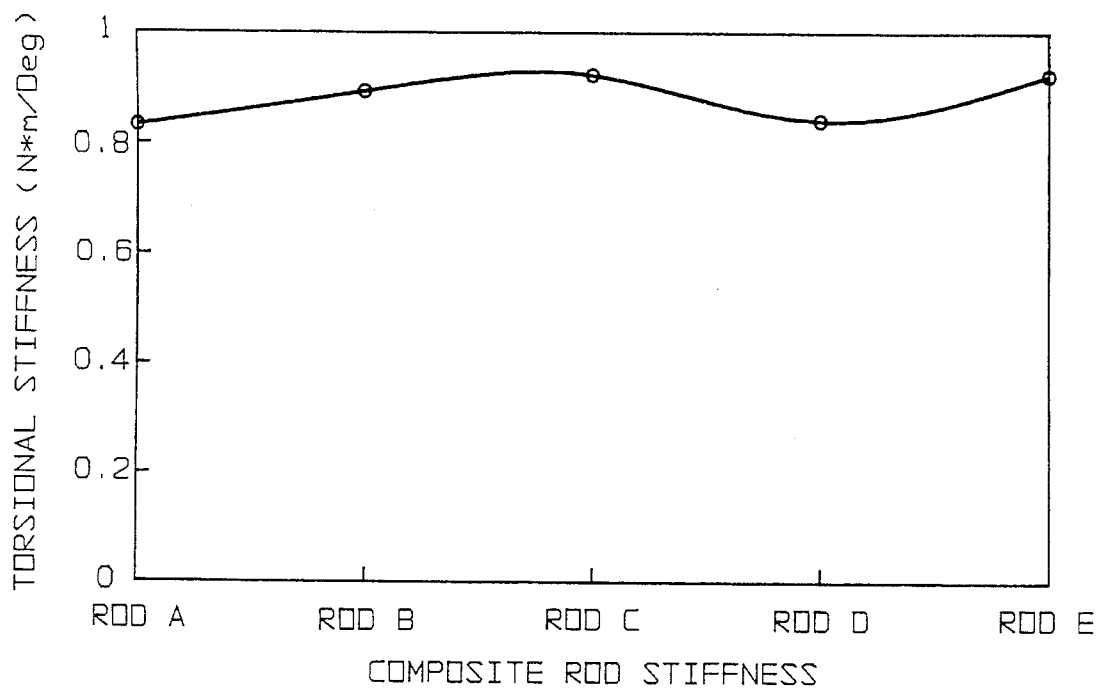
FIG. 4 is a graph illustrating the torsional stiffness of five different embodiments of the composite fixation rod of the present invention.
Figure 5:
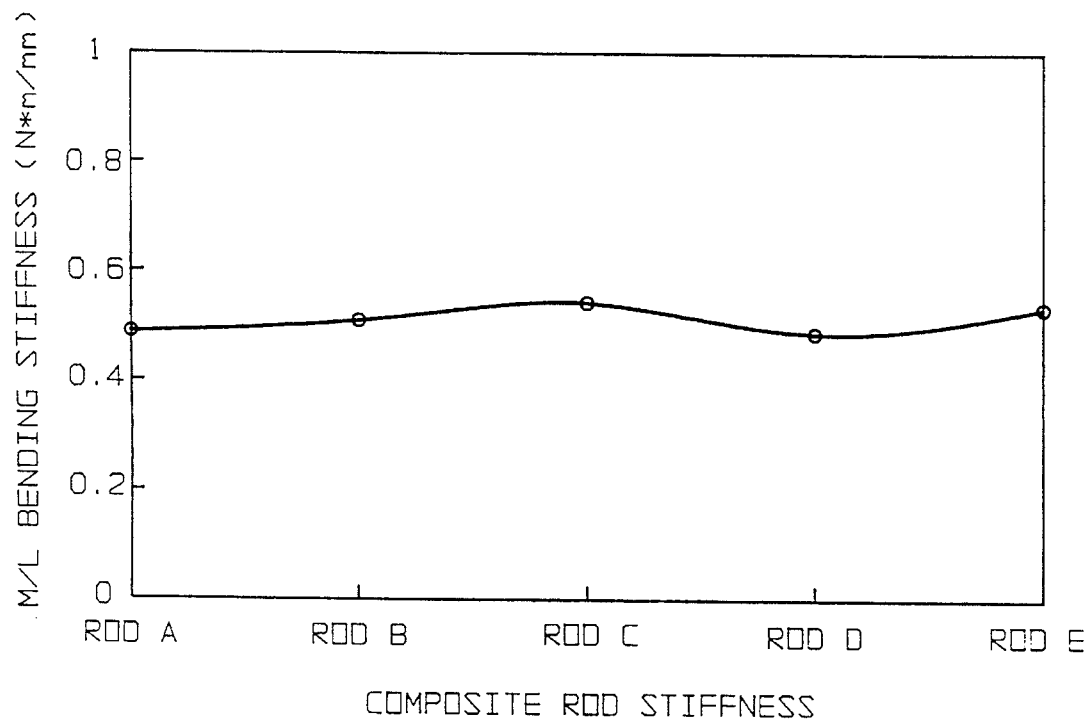
FIG. 5 is a graph illustrating the medial/lateral bending stiffness of the five different composite rods labeled in FIG. 4.
Figure 6:
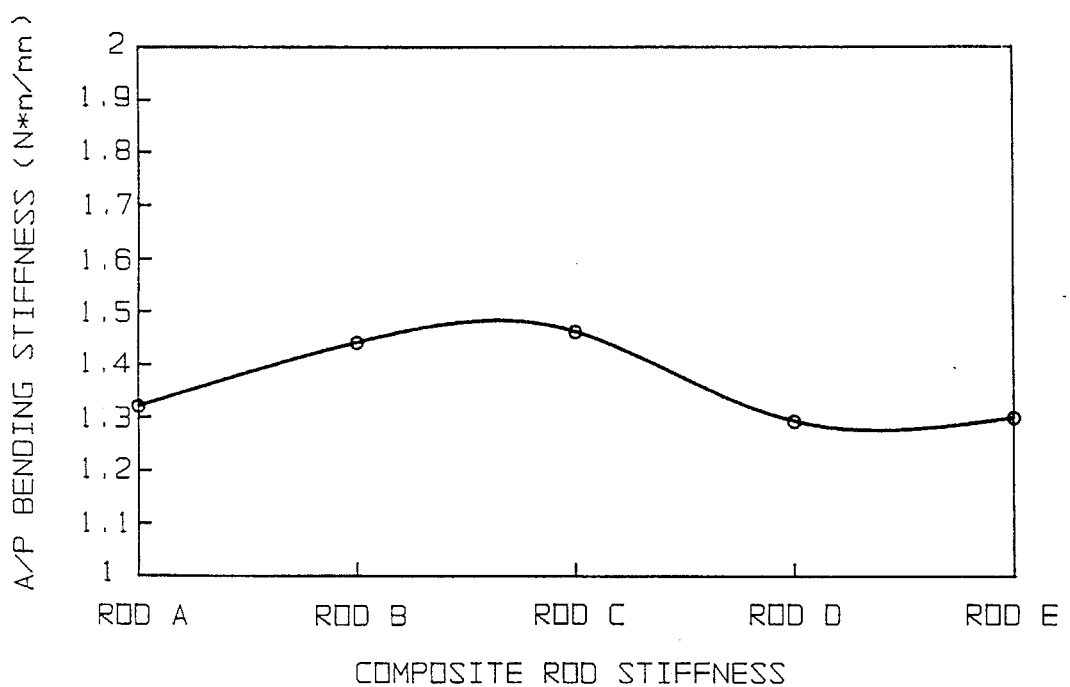
FIG. 6 is a graph illustrating the anterior/posterior bending stiffness of the five different composite rods labeled in FIG. 4.

The data illustrated in FIGS. 4–6 was obtained by attaching the five different fixation rods set forth immediately above to a simulated bone using a plurality of clamp assemblies and fixation pins as described above. The label "M/L Bending Stiffness" in FIG. 5 indicates the medial/lateral bending stiffness of the fixation rods; and the label "A/P Bending Stiffness" in FIG. 6 indicates the anterior/posterior bending stiffness of the fixation rod. The medial/lateral bending stiffness generally corresponds to a direction lying in a plane containing both the simulated bone and the fixation rod.

As indicated by FIGS. 4–6, the stiffness in the torsional, medial/lateral bending and anterior/posterior bending directions does not vary significantly from one composite rod to another. For each of the composite rods A–E shown in FIGS. 4–6, the percentage change for the torsional stiffness and bending stiffness of the composite rods is relatively small when calculated as a percentage change.

Figure 7:
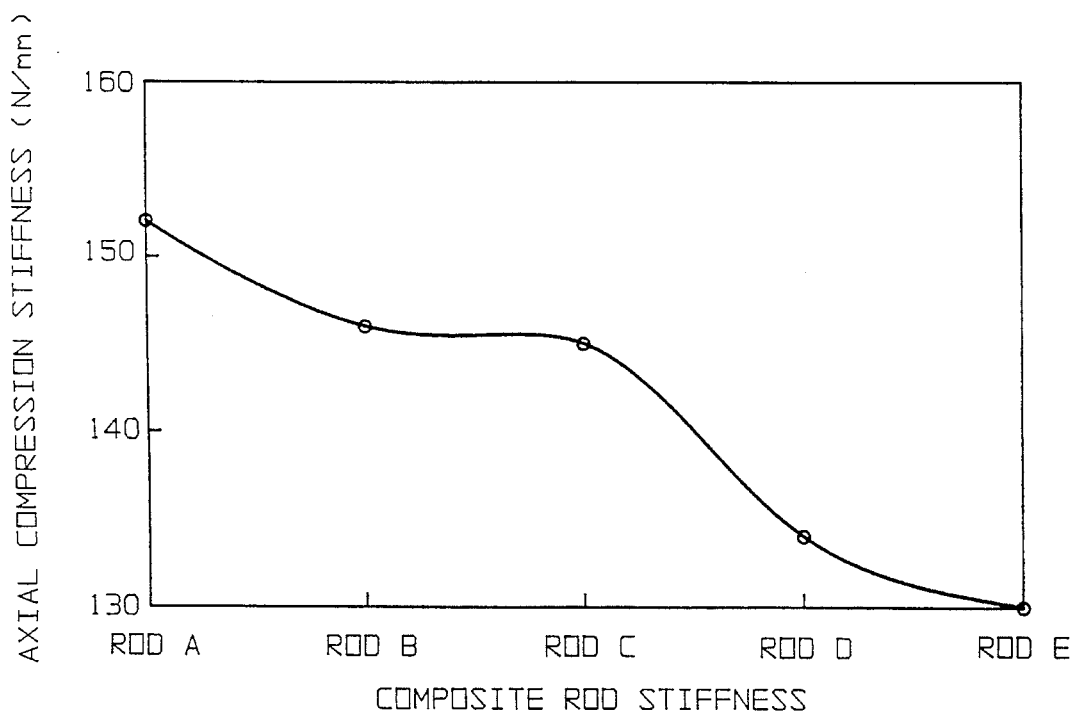
FIG. 7 is a graph illustrating the axial compression stiffness of the five different composite rods labeled in FIG. 4.

Referring now to FIG. 7, it is apparent that the axial compression stiffness varies much more dramatically than the torsional and bending stiffnesses. It is thus possible with the present invention to provide a plurality of fixation rods having the same exterior geometry and which include substantially constant torsional and bending stiffnesses while varying the axial compression stiffness.

Using a composite structure, it is possible to construct a fixation rod of the present invention having a modulus of elasticity of between about $2-20 \times 10^6$ PSI. Bone has a modulus of elasticity of about $2 \times 10^6$ PSI and titanium has a modulus of elasticity of about $16 \times 10^6$ PSI. It is therefore possible with the present invention to select a fixation rod having an axial compression stiffness ranging from that of bone to that of titanium. By providing a more adaptable fixation rod and eliminating the need to adjust the position of the fixation pins relative to the fixation rod, an increased predictability and improved healing process occurs.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A system for external fixation and stabilization of a fracture in a bone, comprising:

a plurality of fixation rods, each said fixation rod having a substantially identical exterior geometry;

at least two fixation pins attachable to the bone; and at least two clamp assemblies, each said clamp assembly interconnecting at least one said fixation pin and a selected one of said fixation rods;

wherein said fixation rods have about the same bending and torsional stiffness from one said fixation rod to another, and have a varying axial compression stiffness from one said fixation rod to another.

2. The system of claim 1, wherein each said fixation rod consists essentially of a non-metallic composite material.

3. The system of claim 2, wherein said composite material includes a plurality of layers, each said layer positioned concentrically about a longitudinal axis of said fixation rod.

4. The system of claim 3, wherein each said layer includes a plurality of fibers having at least one defined orientation relative to said longitudinal axis.

5. The system of claim 1, wherein the varying axial compression stiffness from one said fixation rod to another is of a uniform stepped increment.

6. The system of claim 1, wherein each said fixation rod is essentially radialucent.

7. A method for externally fixating and stabilizing a fracture in a bone, comprising the steps of:

providing a plurality of fixation rods, each said fixation rod having a substantially identical exterior geometry, said fixation rods having about the same bending and torsional stiffness from one said fixation rod to another, and having a varying axial compression stiffness from one said fixation rod to another;

selecting one of said plurality of fixation rods;

connecting at least two clamp assemblies to said selected fixation rod; and attaching at least two fixation pins to said clamp assemblies, respectively, and to the bone on opposite sides of the fracture.

8. The method of claim 7, further comprising the steps of:

disconnecting said clamp assemblies from said selected fixation rod;

selecting another of said plurality of fixation rods; and connecting said clamp assemblies to said another fixation rod.

9. The method of claim 7, wherein said connecting step comprises sliding a body having an opening over said fixation rod.

\* \* \* \* \*